US006051560A

United States Patent [19]
Chang et al.

[11] Patent Number: 6,051,560
[45] Date of Patent: Apr. 18, 2000

[54] CHRONDROITIN SULFATE/SODIUM HYALURONATE COMPOSITION

[75] Inventors: Allison S. Chang, Lesage; James E. Boyd, Barboursville; Richard M. Johnson, Huntington; Harold O. Koch, Barboursville, all of W. Va.

[73] Assignee: Nestle S.A., Vevey, Switzerland

[21] Appl. No.: 07/864,210

[22] Filed: Apr. 3, 1992

Related U.S. Application Data

[63] Continuation of application No. 07/451,073, Dec. 15, 1989, abandoned, which is a continuation of application No. 06/880,957, Jun. 26, 1986, abandoned, which is a continuation of application No. 06/521,575, Aug. 9, 1993, abandoned.

[51] Int. Cl.$^7$ .................................................. A61K 31/70
[52] U.S. Cl. ............................................ 514/54; 536/55.1
[58] Field of Search ............................. 514/54; 536/55.1

[56] References Cited

U.S. PATENT DOCUMENTS

| | | | |
|---|---|---|---|
| 3,405,120 | 10/1968 | Kawano et al. | 260/234 |
| 4,141,973 | 2/1979 | Balazs | 536/55.1 |
| 4,328,803 | 5/1982 | Pape | 424/180 |
| 4,486,416 | 12/1984 | Soll et al. | 514/54 |

OTHER PUBLICATIONS

S.M. Sychkov and S.A. Kuz'mina, Byull. Eksp. Biol. Med., No. 6, 40 (1973) (English language abstract).
S.M. Bychkov and S.A. Kuz'mina, Byull. Eksp. Biol. Med., vol. 83, No. 3, pp. 284–288, Mar. 1977 (English Translation).
S.M. Bychkov and V.N. Kharlamova, Vopr. Med. Khim., No. 3, 269 (1972) (English language abstract).
S.M. Bychkov and V.N. Kharlamova, Biokhimiya, No. 4, 840 (1968) (English translation).
S.M. Bychkov and S.A.Kuz'mina, Byull. Eksp. Biol. Med., vol. 84, No. 11 pp. 562–565, Nov. 1977 (English translation).
S.M. Bychkov, Usp. Sovrem, Biol., 65, 323 (1968) (No translation available).
S.M. Bychkov and S.A. Kuz'mina, Byull. Eksp. Biol. Med., No. 3, 284 (1977) (English language abstract).
M.M. Zakharova and S.M. Bychkov, Byull. Eksp. Biol. Med., No. 12, 1430 (1976) (English language abstract).
T.E. Hardingham and H. Muir, Biochim. Biophys Acta, 279 (1972) pp. 401–405.
Healon Product Monograph—Pharmacia Laboratories, Piscataway, NJ.
E.A. Turley and S. Roth, Nature, vol. 283; Jan. 17, 1980, pp 268–271.
Scott M. MacRae, M.D. et al., American Journal of Ophthalmology 95; pp. 332–341; 1983.
Japan Pharmaceutical Information Center, Tokyo, Japan, "Drugs in Japan" p. 216, 1975, Published on Aug. 10, 1975 by Yakugyo Jiho Co., Ltd. Japan.
Emil Hatschek, *The Viscosity of Liquids*; D. Van Nostrand Company, Inc. New York, 1928; Chapter IX; pp. 135–164.
T.E. Hardingham and H. Muir, Biochem. J., 139, pp. 565–581, (1974).
V.C. Hascall and D. Heinegard, J. Biol. Chem. 249, pp 4232–4241, (1974).
J. D. Gregory, Biochem.J., 133, pp. 383–386, (1973).
T.E. Hardingham and H. Muir, Biochem., J., 135, 905 (1973).
Armand and Balazs, "On the Structure of Ichthyosan Isolated from Tuna Vitreous", Department of Conn. Tissue Research, Boston Biomed. Research Institute, Boston, MA.
Chakrabarti and Balazs, "Conformational Studies of Vitreous Polysaccharides", Boston Biomedical Research Institute, Boston, Mass.

*Primary Examiner*—Ellli Peselev
*Attorney, Agent, or Firm*—Barry L. Copeland

[57] ABSTRACT

Chondroitin sulfate/soduim hyaluronate compositions exhibiting pseudo-plastic behavior and non-Newtonian flow characteristics are disclosed.

14 Claims, No Drawings

CHRONDROITIN SULFATE/SODIUM HYALURONATE COMPOSITION

This application is a file wrapper continuation of prior application Ser. No. 07/451,073, filed on Dec. 15, 1989, now abandoned which is a continuation of Ser. No. 06/880,957, filed on Jun. 26, 1986 (now abandoned), which is a file wrapper continuation of Ser. No. 06/521,575, filed on Aug. 9, 1983 (now abandoned).

FIELD OF THE INVENTION

The invention relates to compositions obtained by adding chondroitin sulfate to sodium hyaluronate in aqueous buffer solution, or sodium hyaluronate to chondroitin sulfate in aqueous buffer solution.

BACKGROUND OF THE INVENTION

This invention relates to compositions for protecting both human and animal endothelial and epithelial cells which are subject to exposure to trauma. More particularly, this invention concerns compositions for protecting endothelial and epithelial cells in anticipation of surgical trauma using chondroitin sulfate/sodium hyaluronate compositions.

Since human corneal endothelial cells are not known to reproduce, it is of vital importance to protect endothelia to prevent cell damage prior to subjection to anticipated trauma, such as surgery. Recent advances in ophthalmic surgery have increased the need to protect corneal endothelial cells which may be subject to irreversible destruction during such surgery. Of particular significance is the need to protect corneal endothelial cells during intraocular lens (IOL) implantation, corneal transplantation and other intraocular surgical operations. Previous work in this field has been directed to protecting corneas with both non-biological and biological polymers.

Macromolecules heretofore employed in the protection of corneas include chondroitin sulfate and sodium hyaluronate. The use of a chondroitin sulfate solution for the protection of corneal surface tissue is described in a "CHONDRON" product monogram, Kakan Pharmaceutical Company, Ltd., Tokyo, Japan, 1981. The use of sodium hyaluronate as an aid in ophthalmic surgery is described in a "HEALON" product monogram, Pharmacia Laboratories, Piscataway, N.J. 1980.

Solutions containing chondroitin sulfate or sodium hyaluronate alone have not met with complete satisfaction due to inadequate corneal dome maintenance which in turn provides spatial separation of cornea endothelium and surgical instruments, etc., or inadequate corneal endothelial cell protection, respectively.

In view of the above, it would be advantageous to prepare a viscous composition containing chondroitin sulfate and sodium hyaluronate, without the use of any other active material which could irritate or damage corneal endothelial cells.

SUMMARY OF THE INVENTION

Viscosity is normally a function of molecular weight at constant solute concentration. It has now been discovered that chondroitin sulfate and sodium hyaluronate may be mixed in aqueous buffer solution in specified ratios to produce a composition having surprisingly high viscosity and offering superior protection to corneal surface cells during intraocular lens implantation, corneal transplantation, and other intraocular surgical operations.

Additionally, the chondroitin sulfate/sodium hyaluronate compositions of the present invention can be administered after trauma as an aid in healing. Surprisingly, it has been found that the chondroitin sulfate/sodium hyaluronate compositions of the present invention exhibit enhanced solution stability and improved physical properties. These compositions are useful for topical applications as well as for irrigation during surgery.

DETAILED DESCRIPTION OF THE INVENTION

Both chondroitin sulfate and sodium hyaluronate are glycosaminoglycans, commonly known as mucopolysaccharides. By mixing chondroitin sulfate and sodium hyaluronate in aqueous solution, it has been surprisingly found that the molecules appear to line up and attract each other by hydrogen bonding in the N-acetylamino group as shown below for a segment of molecular units. The hydrogen bonding interaction is only one of several possible interactions for chondroitin sulfate and sodium hyaluronate.

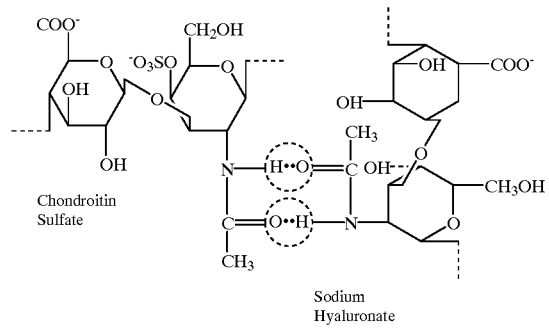

Turley and Roth, Nature, 283, pp. 268–271(1980), have experimentally demonstrated that chondroitin sulfate-derivatized beads and hyaluronate-derivatized beads are capable of binding interaction with each other and have postulated that the interaction occurs between the carbohydrate chains of the polymers.

It has been surprisingly found that addition of chondroitin sulfate to sodium hyaluronate in aqueous solution or sodium hyaluronate to chondroitin sulfate in aqueous solution dramatically increases the viscosity of mixture. This increase in viscosity appears to be mainly due to increase in molecular weight rather than solute concentration increase. As those in the art are aware, viscosity of solute-solvent is a function of molecular weight and concentration of solute. The hydrogen bonding interaction postulated above between chondroitin sulfate and sodium hyaluronate would result in effectively enlarging the molecular size. Thus, viscosity of the mixture would be increased. The following examples demonstrate the nonlinear or synergistic change in physical properties by mixing of chondroitin sulfate and sodium hyaluronate in aqueous solution, which characterize the present invention. In the following examples, chondroitin sulfate is abbreviated CS, and sodium hyaluronate is abbreviated SH.

EXAMPLE

A chondroitin sulfate/sodium hyaluronate solution was prepared by adding 5.3 grams of chondroitin sulfate to 4.2 grams of sodium hyaluronate in 100 ml of water containing 0.15 grams of monobasic sodium phosphate and 0.45 grams of dibasic sodium phosphate with a trace of sodium chloride. The viscosities of the mixture and individual solutions are shown below.

Solution A
5.3 g CS/4.2 SH in 100 ml water with buffer.
Viscosity at 25° C.=71,500 CPS at shear rate less than 2/sec.

Solution B
4.2 g SH in 100 ml water with buffer.
Viscosity at 25° C.=58,700 CPS at shear rate less than 2/sec.

Solution C
5.3 g CS in 100 ml water with buffer.
Viscosity at 25° C.=10 CPS.

A negative reaction (i.e., lack of synergistic change) of chondroitin sulfate with methyl cellulose (MC) is demonstrated by the following example. Two grams of chondroitin sulfate is added to 2 grams of methyl cellulose in 100 ml of water.

The viscosities of mixture and individual solutions are shown below.

Solution D
2 g MC/2 g CS* in 100 ml water.
Viscosity at 25° C.=5,991 CPS at shear rate less than 50 sec.
*CS is insoluble in solution containing over 2 g MC.

Solution E
2 g MC in 100 ml water.
Viscosity at 25° C.=5,857 CPS at shear rate less than 50 sec.

Solution F
2 g CS in 100 ml water.
Viscosity at 25° C.=3.0 CPS.

Due to the molecular structure of methyl cellulose, the —N—C— groups inchondroitin sulfate could not possibly form hydrogen bonds with methyl cellulose. Methyl cellulose lacks —N—C— groups in the molecules. Hence, addition of chondroitin sulfate in methyl cellulose solution results in insignificant increase in viscosity. The observed small increase in viscosity is due to concentration effect only.

Interaction between chondroitin sulfate and sodium hyaluronate is believed to take place at any concentration. However, the synergistic viscosity effect is more pronounced at higher concentration because of concentration effect and closeness of molecules for interaction. The solution of chondroitin sulfate/sodium hyaluronate mixture exhibits non-newtonian flow characteristics and has pseudo-plastic behavior. The viscosity of pseudo-plastic substances decrease with increasing shear rates, i.e., relation of viscosity to shear rate is not linear. The following table shows the viscosity plotted against high shear rate at 25° C. for solution "A".

|  | SHEAR RATES ($sec^{-1}$) | | | |
| --- | --- | --- | --- | --- |
|  | 250 | 500 | 2500 | 5000 |
| Absolute Viscosity, CPS at 25° C. | 1,774 | 1,075 | 307 | 181 |

Most recent data indicate that CS/SH compositions of the invention do not have a yield point.

In the practice of the invention sodium hyaluronate may be used at concentrations from about 0.1 g up to about 10 g in 100 ml water at temperatures between about 4° C. and about 37° C. Chondroitin sulfate is also used at concentrations from about 0.1 g up to about 10 g in 100 ml water at temperatures between about 4° C. and about 37° C. Magnesium, calcium and potassium chondroitin sulfates and hyaluronates are also useful in the practice of the invention. Within the ranges just described, any quantity of chondroitin sulfate can be added to form binding interaction with hyaluronate and produce physical and flow properties suitable for specific pharmaceutical and ophthalmic uses. Adding 12.6 g of chondroitin sulfate to 10 g sodium hyaluronate in water, the resulting solution has viscosity of over 1 million centipoises at 25° C. (for low shear rate below 50 $sec^{-1}$).

The aqueous buffer solution used in the practice of the invention includes monobasic sodium phosphate, dibasic sodium phosphate, and sodium chloride mixed to form an aqueous buffer to maintain pH of about 7 to about 8.0 and osmolarity of 300–350 mOsmol/kg. By raising the buffer concentration of monobasic sodium phosphate and dibasic sodium phosphate, the ionic strength of chondroitin sulfate/hyaluronate solution is increased. The kinetic rate constant of molecule interaction between chondroitin sulfate and hyaluronate is increased by raising ionic strength and temperature. This invention comprises concentrations of dibasic sodium phosphate and monobasic sodium phosphate from 0.1 g/100 ml to 5 g/100 ml and pH range of 7.0 to 8.0 at reaction temperatures between 4° C. and 40° C. The following example shows the effect of buffer on the viscosity or molecular weight of complex molecules for 5.3 g CS/4.2 g SH in 100 ml water:

Buffer 1:
  Dibasic sodium phosphate—4.5 mg/ml
  Sodium dihydrogen phosphate hydrate-1.5 mg/ml
  Viscosity of compositions of the present invention at 1 second and 25° C. is 68,878 cps.

Buffer 2:
  Dibasic sodium phosphate—7.5 mg/ml
  Sodium dihydrogen phosphate hydrate-1.0 mg/ml
  Viscosity of compositions of the present invention at 1 second and 25° C. is 115,011 cps.

The solution of chondroitin sulfate/hyaluronate mixture not only exhibits viscoelastic but also rheopectic behavior (i.e., viscosity increases with time at constant shear rate). At constant shear rate of 100 $sec^{-1}$ for solution A, shear stress increases from 435 pascals to 452 pascals in 3 minutes. Both chondroitin sulfate and hyaluronate are helical straight chain molecules. In highly viscous environments at low temperatures, both molecules have less mobility to align the N-acetylamine groups for mutual interaction. This interaction may take place at a very slow rate. However, the mutual interaction increases with raising of the temperature due to kinetic rate increase and better mobility of molecules to align the N-acetylamine groups for hydrogen bonding. When the mixture is subjected to high shear rate, the molecules are also aligned or oriented for bonding interaction. Thus, the viscosity is increased as the mixture is subjected to high shear rate, and/or increase in temperature, resulting in high molecular weight material.

It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A method for the protection of human or animal ophthalmic endothelial or epithelial cells subject to trauma during surgery which comprises administering a therapeutically effective amount of a stable, viscous, aqueous composition to said cells during surgery, said aqueous composition consisting essentially of a mixture of chondroitin sulfate and sodium hyaluronate in an aqueous buffer, each of said chondroitin sulfate and said sodium hyaluronate being contained in said aqueous buffer in a concentration of about 0.1 to 50 wt. %, said mixture exhibiting a synergistic viscosity which exceeds the sum of the individual viscosities of said chondroitin sulfate and sodium hyaluronate.

2. The method set forth in claim 1, wherein said surgery is intraocular lens implantation surgery.

3. The method of claim 1 wherein ophthalmic endothelial cells are protected.

4. The method according to claim 1, wherein said chondroitin sulfate comprises about 5.3% by weight of the total composition and said sodium hyaluronate comprises about 4.2% by weight of the total composition.

5. A stable, viscous, aqueous composition to protect human or animal endothelial or epithelial cells subject to trauma during surgery, said composition consisting essentially of a mixture of chondroitin sulfate at a concentration from about 0.1 grams to about 10 grams per 100 milliliters of water, and sodium hyaluronate at a concentration from about 0.1 grams to about 10 grams per 100 milliliters of water, in an aqueous buffer, said mixture exhibiting a synergistic viscosity which exceeds the sum of the individual viscosities of said chondroitin sulfate and said sodium hyaluronate.

6. The composition of claim 5 wherein the chondroitin sulfate concentration is between about 0.1% and 50% by weight of the total composition and the sodium hyaluronate concentration is between about 0.1% and 50 % by weight of the total composition.

7. The composition of claim 5, wherein the chondroitin sulfate concentration is about 0.1–5.3% by weight and the sodium hyaluronate concentration is about 0.1–4.2% by weight of the total composition.

8. The method set forth in claim 3, wherein said endothelial cells are corneal endothelial cells.

9. A stable, viscous, buffered aqueous solution which comprises a mixture of chondroitin sulfate at a concentration of about 0.1 to 50 wt. % and sodium hyaluronate at a concentration of about 0.1 to 50 wt. %, said mixture exhibiting a synergistic viscosity effect which is sufficient to exceed the sum of the individual viscosities of said chondroitin sulfate and said sodium hyaluronate.

10. A solution according to claim 9, wherein said solution exhibits enhanced solution stability, non-Newtonian flow characteristics and pseudo-plastic behavior, and is maintained at a pH of about 7.0 to 8.0.

11. A solution according to claim 10, wherein the solution has an osmolarity of from about 300 to about 350 mOsmol/kg.

12. A method for the protection of human or animal ophthalmic endothelial or epithelial cells from trauma during surgery, which comprises administering to said cells during surgery, a therapeutically effective amount of a viscous, aqueous solution of claim 9.

13. A method according to claim 1, wherein said mixture of chondroitin sulfate and sodium hyaluronate is formed by mixing chondroitin sulfate and sodium hyaluronate without use of other active materials.

14. A composition according to claim 5, wherein said mixture of chondroitin sulfate and sodium hyaluronate is formed by mixing chondroitin sulfate and sodium hyaluronate without use of other active materials.

* * * * *